United States Patent
Chang et al.

(10) Patent No.: US 6,299,649 B1
(45) Date of Patent: Oct. 9, 2001

(54) UNBALANCED PROSTHETIC DEVICE FOR PROVIDING SIDE-DEPENDENT TWISTING-ROTATIONAL AXIAL-LOADING COUPLING

(76) Inventors: Fu-Kuo Chang, 739 San Rafael Pl., Stanford, CA (US) 94305; Hasan Yildiz, Karadenik Mah 1151 Sok, No. 19 G. O. P. Istanbul (TR); Stuart B. Goodman, 420 Azalea Ave., Los Altos, CA (US) 94022

( * ) Notice: Subject to any disclaimer, the term of this patent is extended or adjusted under 35 U.S.C. 154(b) by 0 days.

(21) Appl. No.: 09/360,926

(22) Filed: Jul. 26, 1999

Related U.S. Application Data

(63) Continuation-in-part of application No. 08/493,502, filed on Jun. 22, 1996, now abandoned.

(51) Int. Cl.$^7$ ........................................................ A61F 2/36
(52) U.S. Cl. ..................... 623/23.34; 623/23.44; 623/23.51
(58) Field of Search ............... 623/16.11, 20.36, 623/23.32, 23.34, 23.44, 23.51

(56) References Cited

U.S. PATENT DOCUMENTS

| | | | |
|---|---|---|---|
| 4,892,552 | * 1/1990 | Ainsworth et al. | 623/23 |
| 4,902,297 | * 2/1990 | Devanathan | 623/16 |
| 5,064,439 | * 11/1991 | Chang et al. | 623/66 |
| 5,163,962 | * 11/1992 | Salzstein et al. | 623/23 |
| 5,181,930 | * 1/1993 | Dumbleton et al. | 623/23 |
| 5,522,904 | * 6/1996 | Moran et al. | 623/23 |

* cited by examiner

*Primary Examiner*—Paul B. Prebilic
(74) *Attorney, Agent, or Firm*—Bo-In Lin

(57) ABSTRACT

The present invention discloses a side-dependent prosthetic device. The side-dependent prosthetic device is a composite prosthetic device with a longitudinal direction. The composite prosthetic device includes a plurality of plies wherein each ply being composed of a plurality of reinforced fibers aligned in a ply orientational angle θi relative to the longitudinal direction of the prosthetic device, where i=1,2,3, . . . ,N and N being the number of the plies. The plurality of plies are laminated together for forming the prosthetic device wherein the ply orientational angles being arranged such that $\theta_1+\theta_2+\theta_3+\ldots+\theta_N \neq 0$ thus forming an unbalanced composite prosthetic device. In another preferred embodiment, the ply orientational angles θi forming a sequence which is represented by $((\theta^1/\theta^2)_s)_n$ where a first ply with orientational angle $\theta^1$ being followed by a second ply with orientational angle $\theta^2$ wherein such a sequence repeated n-times and arranged to be symmetrical to a mid-plane, wherein $\theta^1$ being an angle close to $-10_i$ and $\theta^2$ being an angle close to $-20_i$.

5 Claims, 11 Drawing Sheets

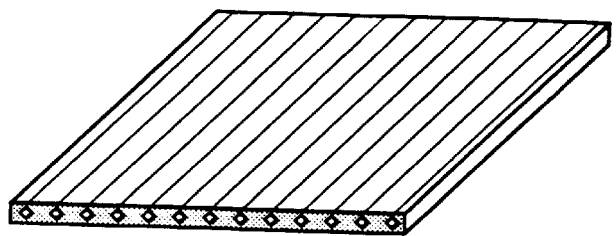
FIG. 2A
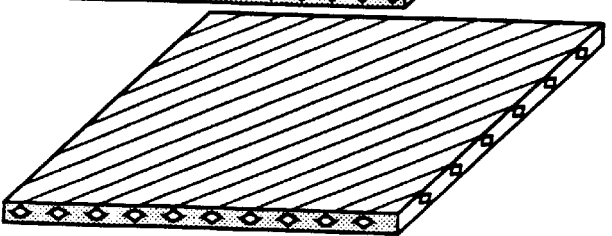
FIG. 2B
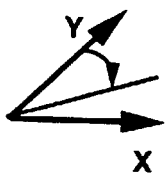
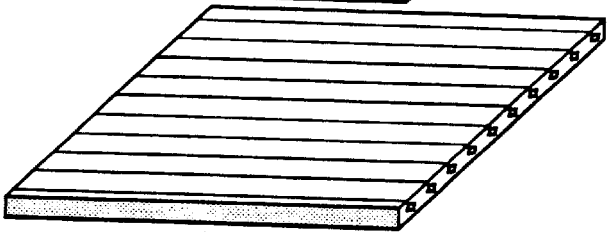
FIG. 2C
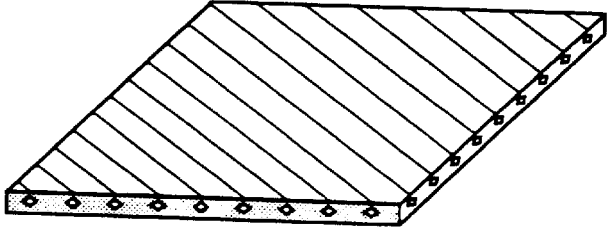
FIG. 2D
TYPICAL PLY LAYUP SEQUENCE
(Prior Art)

FIG. 6 Comparison of the Stiffness of Hip Implants

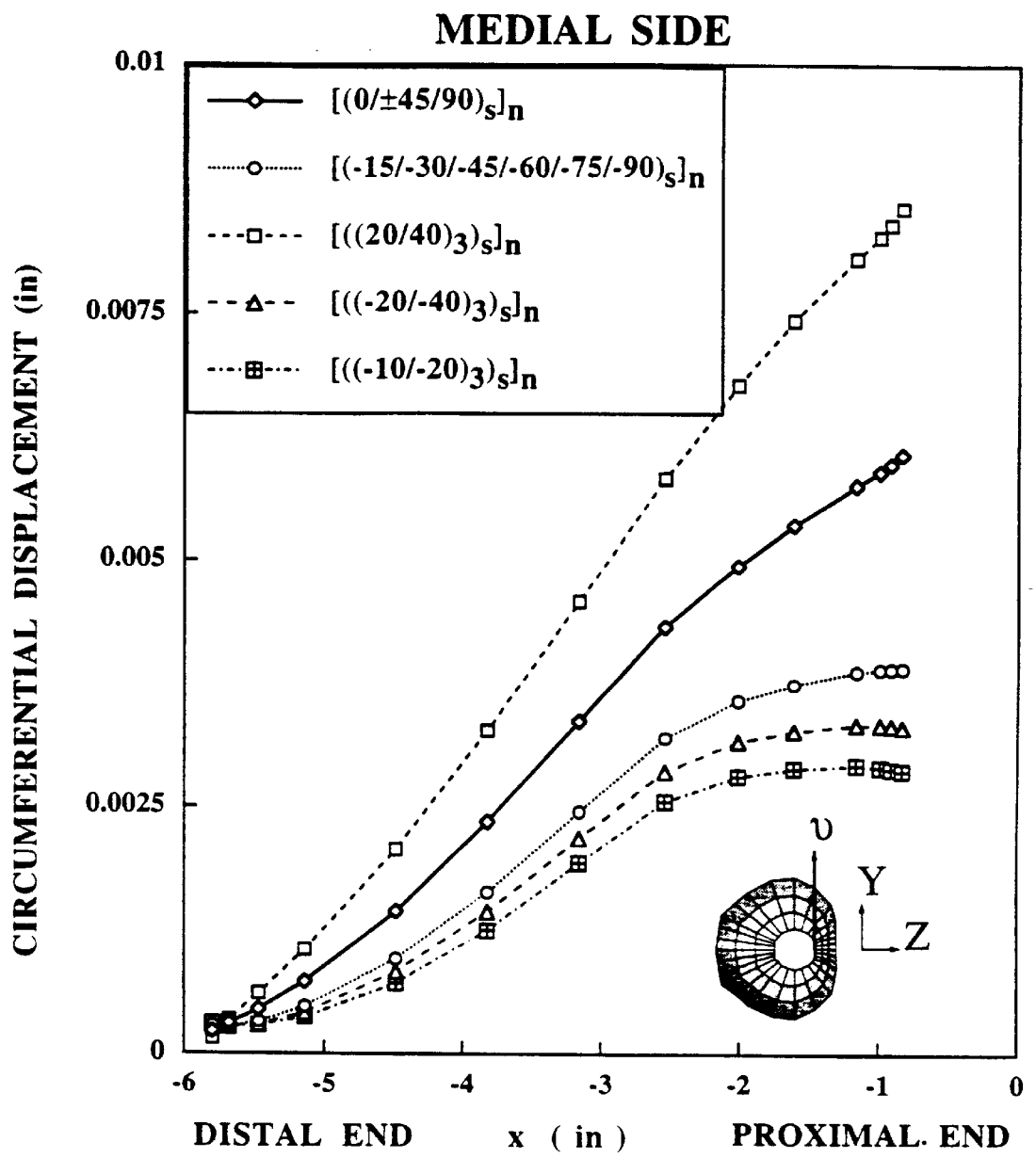
FIG. 8 Circumferential Displacement of Unbalanced Ply Orientations at Medial Bone/Prosthesis Interface (Case 1-Arbitrary)

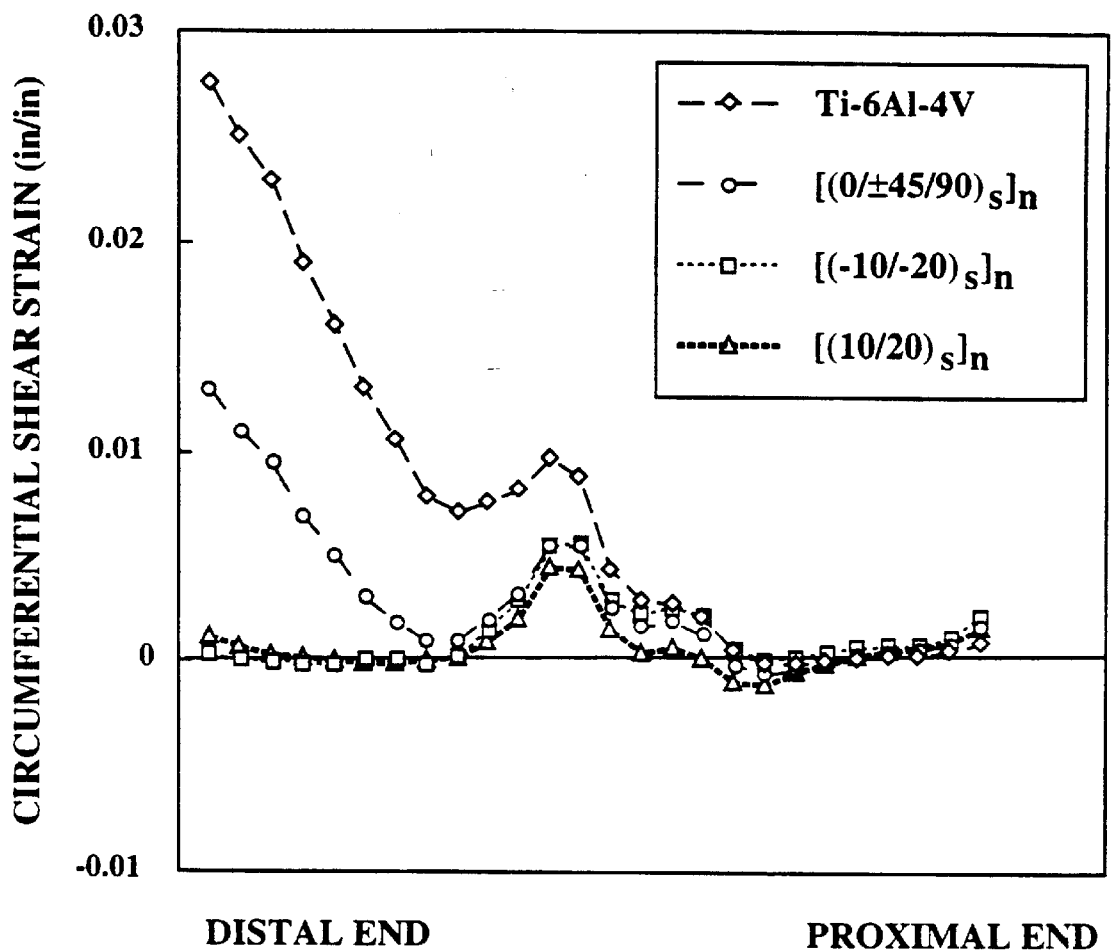
FIG. 9 Circumferential Shear Strain at Medial Bone/Prosthesis Interface (Case 2-Heel Strike)

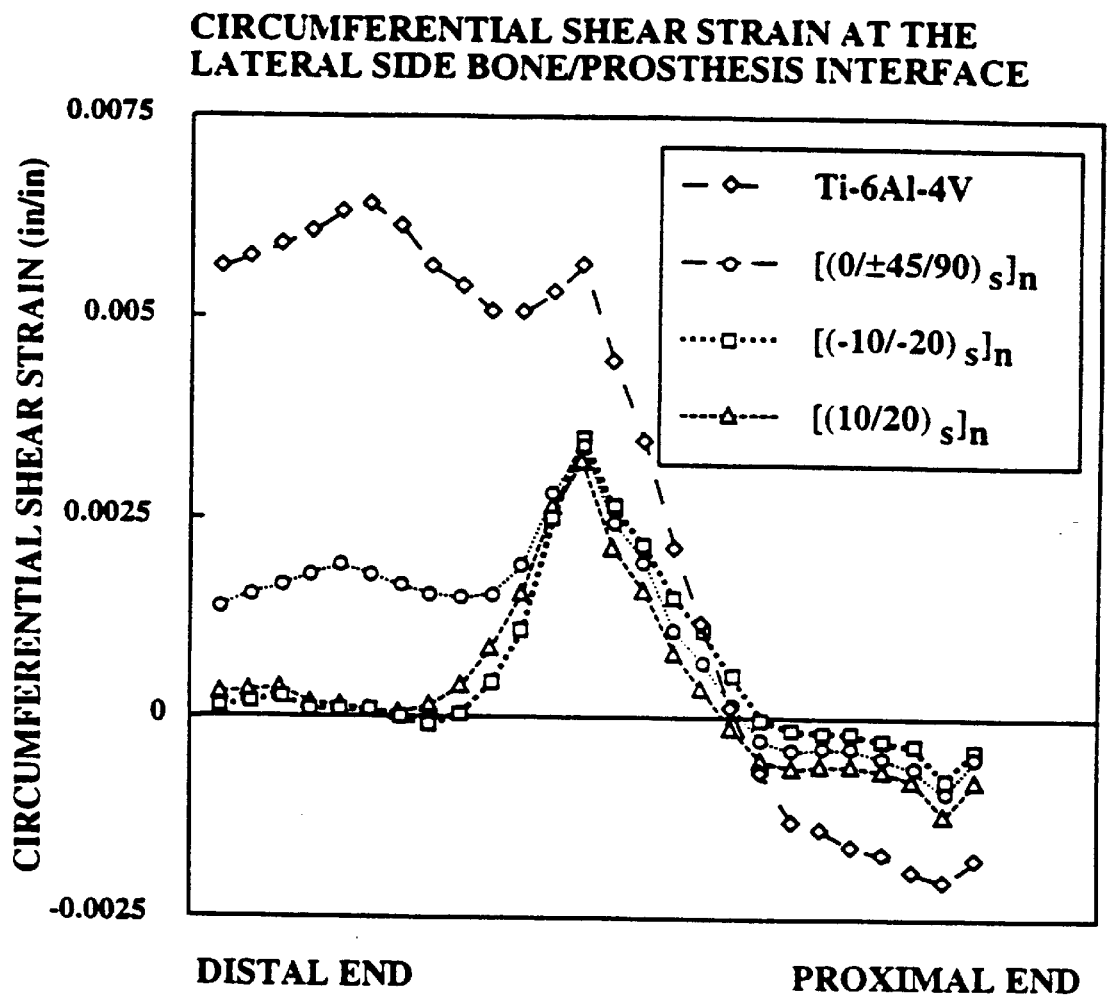
FIG. 10 Circumferential Shear Strain at Lateral Bone/Prosthesis Interface (Case 2-Heel Strike)

UNBALANCED PROSTHETIC DEVICE FOR PROVIDING SIDE-DEPENDENT TWISTING-ROTATIONAL AXIAL-LOADING COUPLING

This is a Continuation in Part (CIP) Application for a pending prior Application with Ser. No. 08/493,502 filed originally on Jun. 22, 1996 now abandoned.

BACKGROUND OF THE INVENTION

1. Field of the Invention

This invention relates generally to the load bearing prosthetic device suitable for human implant. More particularly, this invention relates to side-dependent prosthetic device fabricated by the use of anisotropically oriented fiber composites to reduce stress shielding and micromotion caused by mismatch of bone/stem properties whereby the stem loosening may be minimized.

2. Description of the Prior Art

Even that total hip replacement using artificial components is an established procedure in orthopedic surgery, there are still major concerns for micromotions and stress shielding resulting from mismatch of bone and stem properties causing stem loosening in clinical studies. More details of the studies are published by Huisides, R, et al. (please refer to Clinical Othop., 274:124–134, 1992). Materials such as stainless steel, cobalt chrome alloy and titanium alloy are commonly used for the design and fabrication of artificial hip prostheses either with or without self curing cement. Recently, uncemented press-fit fixation with low modulus hip stem is being used increasingly as an alternative method to cemented joint replacement due to difficulties experienced with the cemented prostheses. Without the use of cement, bonding at the prosthesis-bone interface is becoming important for the initial fixation as well as long term stability. For that reason, use of different materials, including the advanced fiber-2 reinforcement composite materials for prosthesis application have been actively investigated explored. Because the research in this area is relatively new, there are only few published studies in this field. However, no studies have been performed yet to evaluate the effect of fiber orientation of a composite hip implant on the response of the femoral bone. The clinic studies suggested that mismatch of bone and stem properties often are caused by the side-dependent motion and structural characteristics of the stem when the prosthetic devices are applied for a hip implant. However, none of the prior art techniques provide a solution to these concerns. Specifically, several US patents are issued applying fiber composite materials for fabrication of orthopedic devices. However, as explained below, these inventions employ typical balanced composite materials. These types of prostheses would be adequate for applications to replace parts of the body, e.g., neck or spine segments, where no side-dependent considerations are required.

Please refer to FIGS. 1A for a perspective view of a prosthesis that includes a shaft and a neck. FIG. 1B is an explosive view of a segment of the laminated composite hip prosthesis of FIG. 1A. FIG. 1C is an enlarged cutoff explosive view of a small segment of the laminated composite hip prosthesis of FIG. 1A showing the orientation of the plies of the composite. According to FIG. 1C, the prosthesis is a balanced composite hip prosthesis. The prosthetic device has an elongated direction along the shaft of the prosthesis. The orientation of the fiber composites is denoted as positive angle along a counterclockwise direction and a negative angle along a clockwise direction. The neck is therefore oriented along an acute positive direction. The balanced composite is fabricated by laminating a plurality of layers as that shown in FIG. 2. The composites are fabricated by laminating multiple layers wherein each layer is generally referred to as a ply and the fibers in each layer is called the ply orientation of the layer. The sequence of ply orientation of the plies in a composite through the thickness is referred to as stacking sequence. Laminated composite structures can be categorized according to their stacking sequence. The laminates, which are constructed by placing the laminae symmetrically with respect to the mid-plane, are often termed symmetric laminates. The ply orientations of the layers on one side of the mid-plane are a mirror image of the ply orientations on the other side. The symmetric laminates are commonly constructed to simplify their analysis and to eliminate the bending inplane coupling. When all of the plies in a laminate having a counter ply with an opposite sign, as that shown in FIGS. 1 and 2, the laminate is referred to as balanced. A balanced laminate has equal number of plies with positive and negative orientations while the unbalanced laminate does not have equal numbers of plies that have positive and negative orientations to offset each other.

In U.S. Pat. No. 5,064,439, (issued on Nov. 12, 1991) entitled "Orthopedic Device of Biocompatible Polymer with Oriented Fiber Reinforcement", Chang et al. disclose an orthopedic device such as a hip stem with longitudinal curved body fabricated with biocompatible polymer with oriented fiber reinforcement. The reinforcing fibers are continuous filament fiber plies with parallel oriented fibers in each ply. The plies are curved longitudinally to approximately correspond to the curve of the body. The fiber orientation is balanced by providing a ply of negatively angled offset fibers of similar angle for each positively angled offset ply. The device is made by molding plies preimpregnated with polymer prepregs simultaneously by molding a plurality of prepregs into segments which are then molded together, or by molding a segment and incrementally molding additional layers of prepregs thereto in a series of progressive lager molds. This "balanced" device has the difficulties that stress and deformations caused by unbalanced or side-dependent loading are not taken into account for designing and applying the prosthetic devices.

Salzstein et al. disclose in another U.S. Pat. No. 5,163,962 entitled "Composite Femoral Implant Having Increased Neck Strength" a femoral implant for a hip prosthesis using a longitudinal shaft having a neck extending therefrom at an acute angle θ to the longitudinal direction. The prosthesis is made of layers of carbon fiber in a polymeric matrix, each layer containing unidirectional fiber and the layer arranged such that carbon fibers are oriented in the longitudinal direction and the ±θ direction. The improvement of this invention involves balancing at least 50% of the layers in the ±θ direction. An example of the stacking sequence is defined as $[-18_i,+18_i,+40_i,-40_i,0_i,+40_i,-40_i,0_i]_{ns}$ where ns is used to indicate that it is not symmetrical to the mid-plane layer. Such implant is still a balanced composite and does not offer a solution to the side dependent effects discovered in the hip replacement prostheses.

Dumbleton et al. disclose in another U.S. Pat. No. 5,181, 930 (issued on Jan. 26, 1993), entitled "Composite Orthopedic Implant", a beam adapted for implantation within a bone for supporting bending and torsional loading forces. The beam has a stiffness defined by a modulus elasticity wherein the stiffness varies along the length of the beam to match the corresponding stiffness of the cortical bone adjacent the beam after implantation within the bone. The beam is made with elongated core formed of continuous filament carbon fibers embedded in a thermoplastic polymer matrix with the carbon filaments extending in a direction substantially parallel to the longitudinal axis of the beam.

Balanced fiber composites are employed in these patents. As explained earlier, when the implanted device is for a side-dependent operation such as a hip implant, the prosthetic device are subject to anisotropic forces which depends on the right or left sides of the implant The side dependent effect can cause mismatches and generate micromotions and stress shielding if the prosthetic device is designed without taking the side-dependent effects into considerations. The orthopedic implant devices mentioned above which uses balanced fiber reinforcement for fabrication cannot resolve these difficulties.

In another U.S. Pat. No. 5,522,907, Moran et al. disclose an unbalanced composite where two fiber orientations are used to form an unbalanced composite femoal implant for a hip prosthesis. Moran's prosthesis is made with at least 50% of the fibers of the composite pliers oriented in the θ direction that is the direction of the neck relative the longitudinal direction aligned with the shaft as that described in column 2, lines 24–33. In one example, as that presented in column 6, lines 7–30, Moran et al. show that when the neck is 40° relative to the shaft, the fibers are arranged to have at least 50% to be oriented at 40°. The angle of the neck is independent of side. According all the independent claims of Moran, the fibers are oriented to align with the direction of the neck. By arranging at least 50% of the fibers to orient along the neck direct θ, the prosthetic device of Moran does not address issues caused by the side-specific load and stress conditions. Specifically, Moran's device does not address the difficulties caused by a twisting and rotating axial-loading that is side-dependent. Due to the fact that the relative angle θ of the neck angle relative to the shaft is substantially the same for left and right side application, there is very little correlation with the side-specific loading conditions. Therefore, the device disclosed by Moran cannot resolve the problems of stress and deformations caused by relative micro-motions resulted from the side-dependent twisting and rotational axial loading.

Therefore, there is still a need in the art of prosthetic device design and manufacture by the use of composites to provide improved techniques to overcome these difficulties. Specifically, the new design and manufacture techniques must provide a prosthetic device which can offset the side dependent unbalanced effects to minimized the mismatches encountered in the conventional orthopedic implants for applications such as total hip replacement.

SUMMARY OF THE PRESENT INVENTION

It is therefore an object of the present invention to provide a prosthetic device and fabrication method, which is unbalanced in nature and side-dependent in order to overcome the aforementioned difficulties, encountered in the prior art.

Specifically, it is an object of the present invention to provide a prosthetic device and fabrication method wherein the prosthetic device are fabricated by use of an-isotropic orientations of the fiber composites. The prosthetic device is formed to provide side-dependent coupling of twisting and rotational axial loading. The prosthetic device is able to offset the side-dependent effects whereby the micro-motion and stress shielding and caused by the mismatch due to side-dependent effects are minimized.

Another object of the present invention is to provide a prosthetic device and fabrication method wherein the design steps are disclosed. The design method is to determine the orientations of prosthetic composites by taking into account of geometric variations and ply drop-offs due to termination. The fiber orientations are also determined by taking into consideration the side-dependent coupling of the twisting and rotational axial loading. The fiber composites can be best utilized to tailor fit the implant variations and to minimize the side-dependent stress and deformation caused by the twisting and rotational axial loading.

Another object of the present invention is to provide a prosthetic device and fabrication method wherein the design steps are disclosed to determine the orientations of prosthetic composites. The design method also accounts for the corresponding stress energy density (DEN) for the bone such that a long-term bone maintenance program can be properly established and implemented.

Briefly, in a preferred embodiment, the present invention comprises an side-dependent prosthetic device. The side-dependent prosthetic device is composite prosthetic device with a longitudinal direction. The composite prosthetic device includes a plurality of plies wherein each ply being composed of a plurality of reinforced fibers aligned in a ply orientational angle θi relative to the longitudinal direction of the prosthetic device, where i=1,2,3, . . . ,N and N being the number of the plies. The plurality of plies being laminated together for forming the prosthetic device wherein the ply orientational angles being arranged such that a sum of all the ply orientation angles represented by (θ1+θ2+θ3+ . . . +θ$_N$) is not zero thus forming an unbalanced composite prosthetic device. In another preferred embodiment, the ply orientational angles θi forming a sequence which is represented by $((\theta^1/\theta^2)_s)_n$ where a first ply with orientational angle $\theta^1$ being followed by a second ply with orientational angle $\theta^2$ wherein such a sequence repeated n-times and arranged to be symmetrical to a mid-plane, wherein $\theta^1$ being an angle close to $-10_i$ and $\theta^2$ being an angle close to $-20_j$.

These and other objects and advantages of the present invention will no doubt become obvious to those of ordinary skill in the art after having read the following detailed description of the preferred embodiment which is illustrated in the various drawing figures.

BRIEF DESCRIPTION OF THE DRAWINGS

FIG. 2A to 2D are perspective views of four layers of fiber reinforced laminated composite of a prior art balanced prosthesis;

FIG. 8 shows the circumferential displacements of unbalanced ply orientation at medial bone and prosthesis interface;

FIG. 9 shows the circumferential shear strain at medial bone and prosthesis interface;

FIG. 10 shows the circumferential shear strain at lateral bone and prosthesis interface.

DETAILED DESCRIPTION OF THE PREFERRED EMBODIMENT

Figures 1A, 1B, 1C:
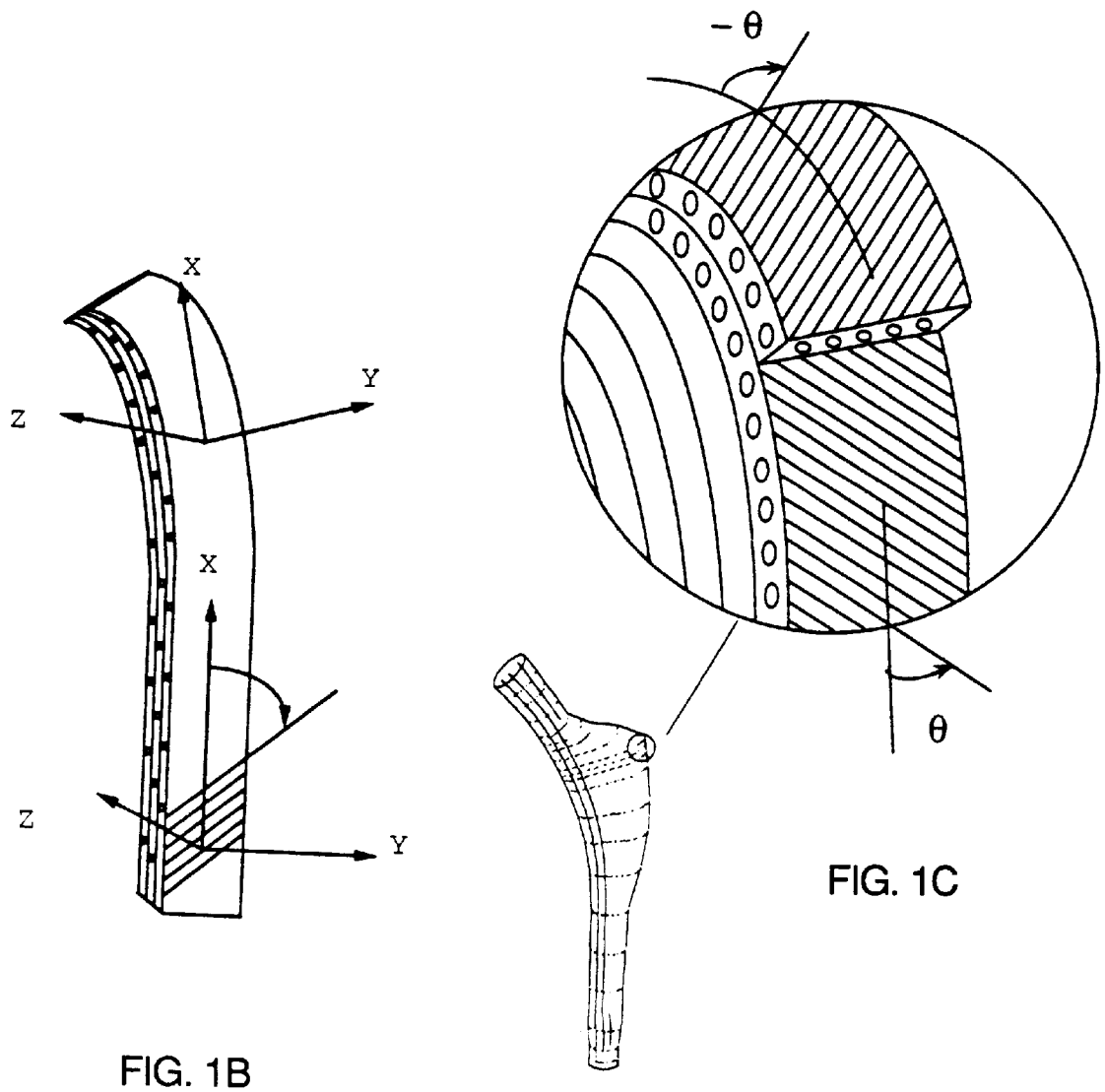
FIG. 1A is a perspective view of a laminated composite hip prosthesis includes a shaft and a neck.
FIG. 1B is an explosive view of a segment of the laminated composite hip prosthesis of FIG. 1A.
FIG. 1C is an enlarged cutoff explosive view of a small segment of the laminated composite hip prosthesis of FIG. 1A showing the orientation of the plies of the composite.
Figure 3A:
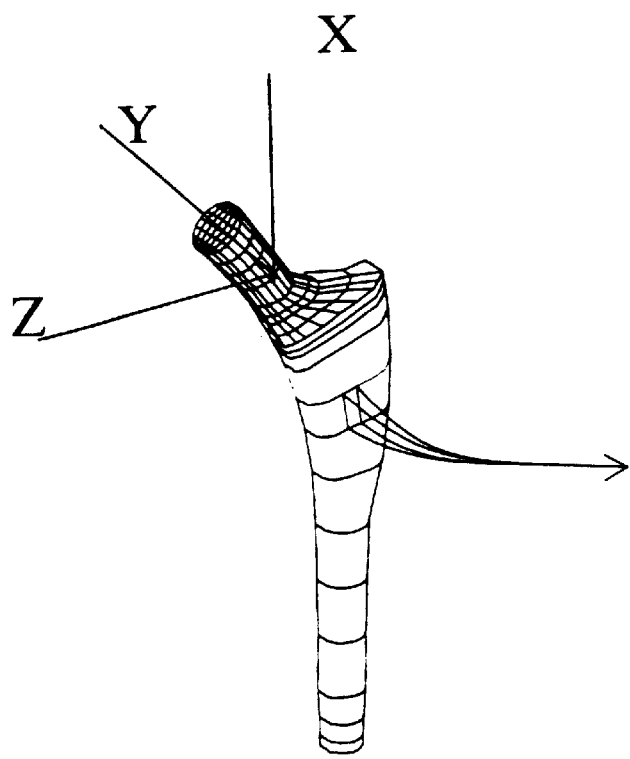
FIG. 3A is a perspective view of a composite hip implant.
Figure 3B:
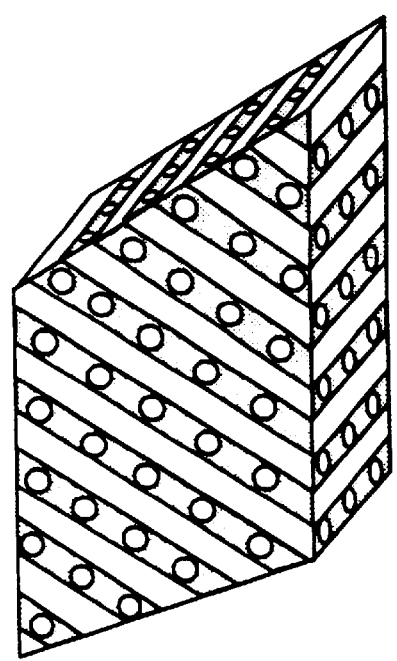
FIG. 3B is a three dimensional eight node composite elements for carrying out a finite element analysis.
Figure 4A:
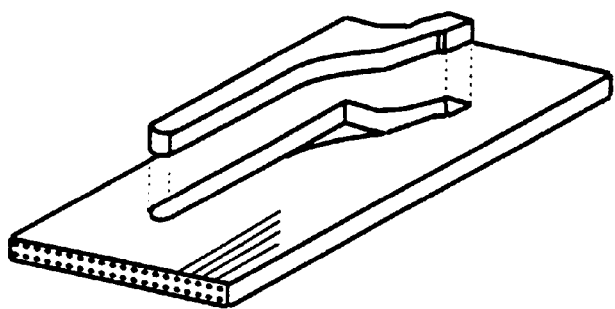
FIG. 4A is a perspective view of a composite prosthesis manufactured by laminating multiple flat plates.
Figure 4B:
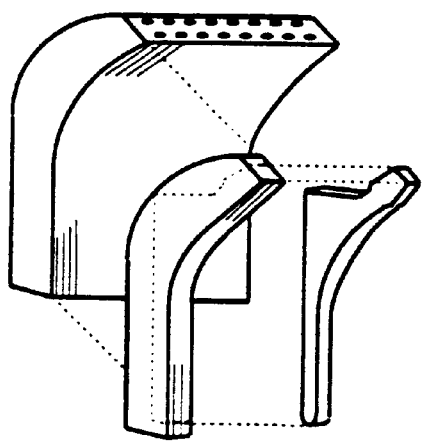
FIG. 4B is a perspective view of a composite prosthesis manufactured by laminating multiple bend plates.

In view of the difficulties of conventional prosthetic devices using the balanced and unbalanced composite fibers discussed above, the present invention teaches the use of a novel and non-obvious application of unbalanced and side-dependent angular-inclined fiber composite materials for the fabrication of prosthetic devices. The mechanical performance of fiber reinforced composite hip prostheses in a femur is dependent on the fiber orientation of a composite femur implant on the response of the surrounding femoral bone. Referring to FIGS. 3A and 3B for a composite hip prosthetic device 100 in a femur and a composite element shown as a three-dimensional multiple-node element for strain-stress analysis of the present invention. The prosthetic device 100 is made of a plurality of unidirectional composite plies with drop-off points where the plies terminate. There are two methods for manufacturing the composite prosthetic device 100. These two methods are illustrated in FIG. 4. The first method is a flat plate method where the unidirectional plies are stacked upon a flat plate until the maximum anterior-posterior thickness for the prosthesis has reached. The second method is a bend plate method where the prosthetic device 100 is fabricated by laying each of these composite plies on a female mold with the inner contour matches the medial curvature of a stem. In a preferred embodiment of present invention, the composite is composed of an AS4-PEEK graphite thermoplastic unidirectional material. A zero directional fiber orientation is defined as the fiber parallel to the axial direction along the elongated shaft of the implant from the distal end to the center of the femoral head.

Figure 5:
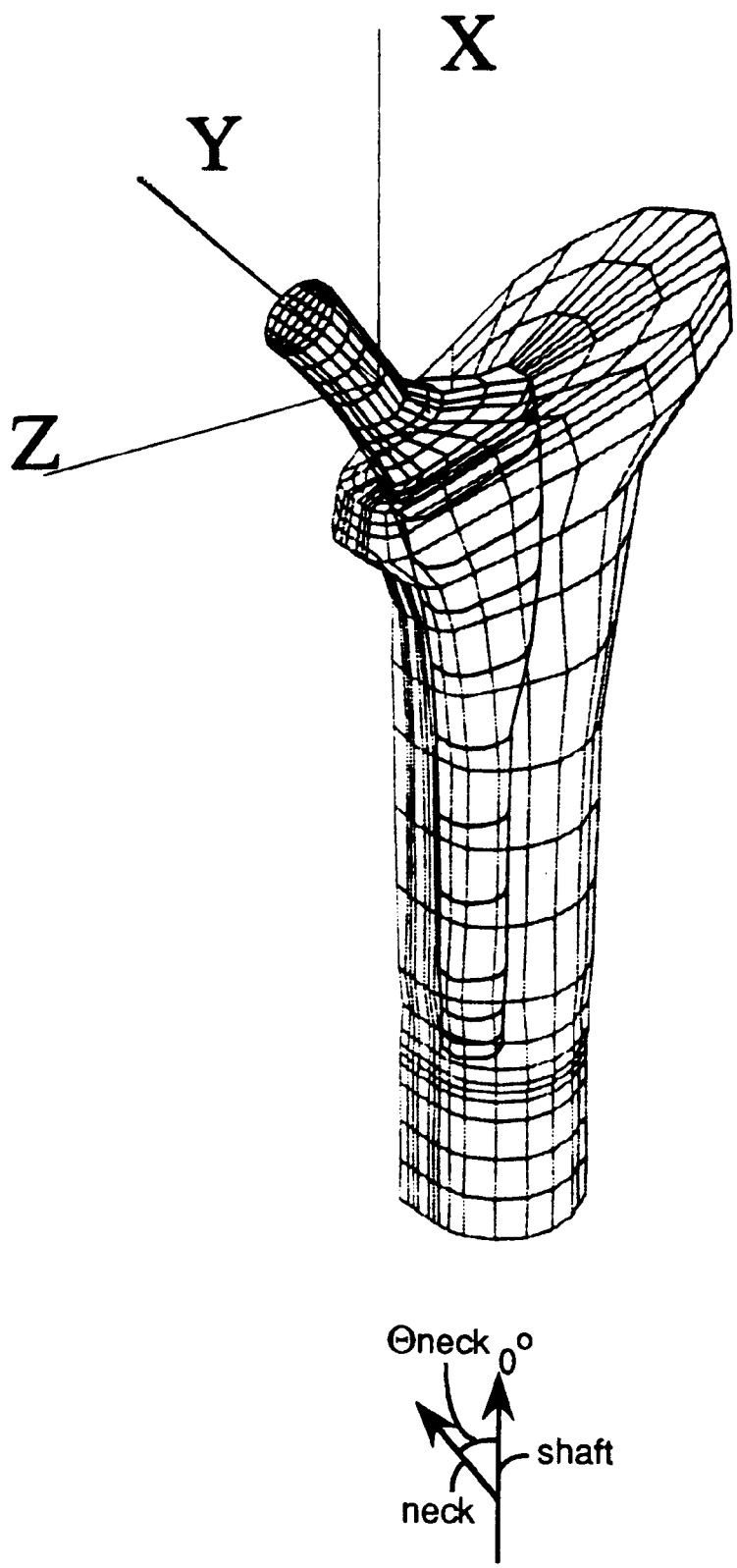
FIG. 5 is a perspective view of a typical finite element stem-femur mesh used in a loading analysis calculation.
Figure 6:
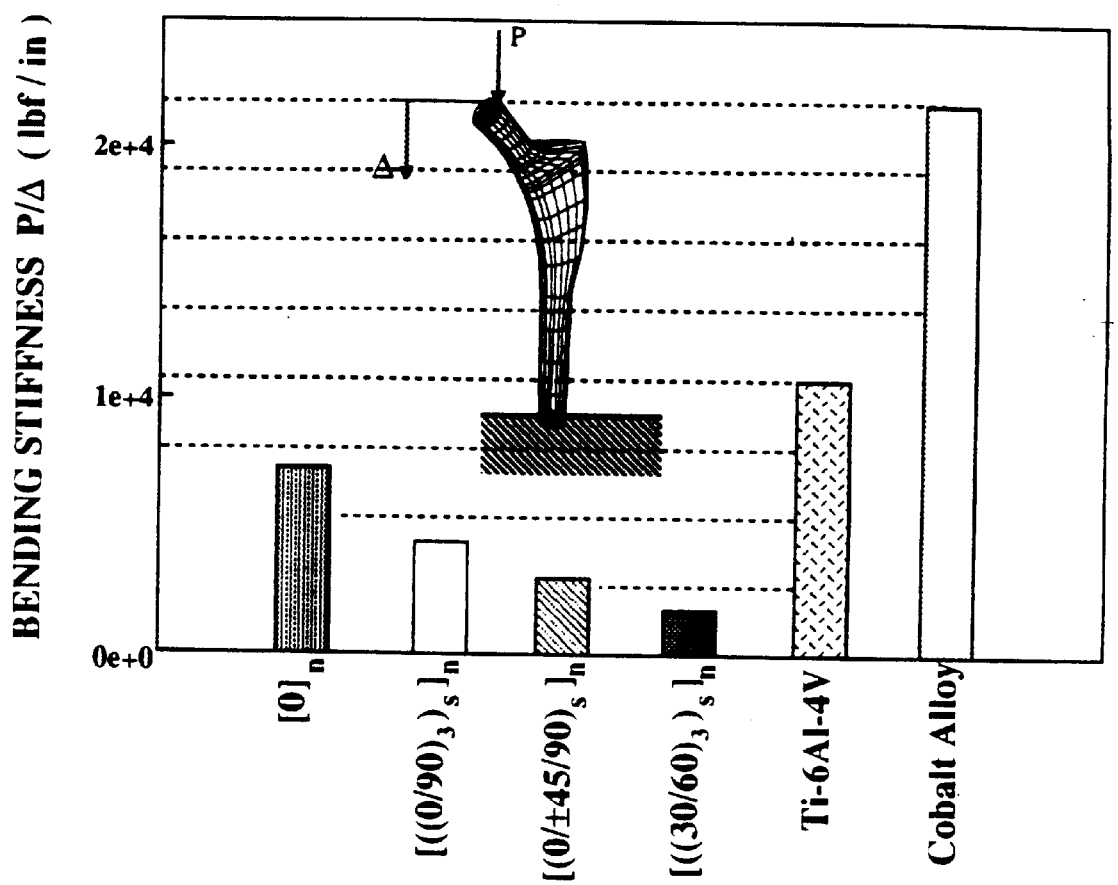
FIG. 6 is a perspective view of a typical finite element stem-femur mesh.

In order to determine a ply orientation and the variation of material properties for each ply to best fit the implant geometry in fabrication of the composite prostheses, a design process is taught by this invention taking advantage of the an-isotropical nature of the fiber composite plies. The geometrical variations and ply drop-off points due to ply termination are taken into account by employing a special brick finite element to analyze a thick composite. FIG. 5 shows the mesh elements used for the finite element analysis. The mechanical responses of the composite prosthetic device 100 are a function of the ply orientations. According to conventional orientation denotation, the prosthetic device has an elongated direction along the shaft of the prosthesis. The orientation of the fiber composites is denoted as positive angle along a counterclockwise direction and a negative angle along a clockwise direction. The neck is therefore oriented along an acute positive direction. The stiffness of the composite prosthesis and a metallic implant is compared in FIG. 6. It is dearly shown that the stiffness of the prosthesis varies within a wide range from 15% to 70% of the bending stiffness of titanium prosthesis depending on the ply orientation. The implant composite is composed of a graphite/PEEK thermoplastic composite. Compared to a metallic prosthetic device with fixed stiffness once the material and geometry are defined, design of a composite prosthetic device offers greater degree of flexibility by changing the stiffness of a composite prosthesis by varying the ply orientations.

Figure 7:
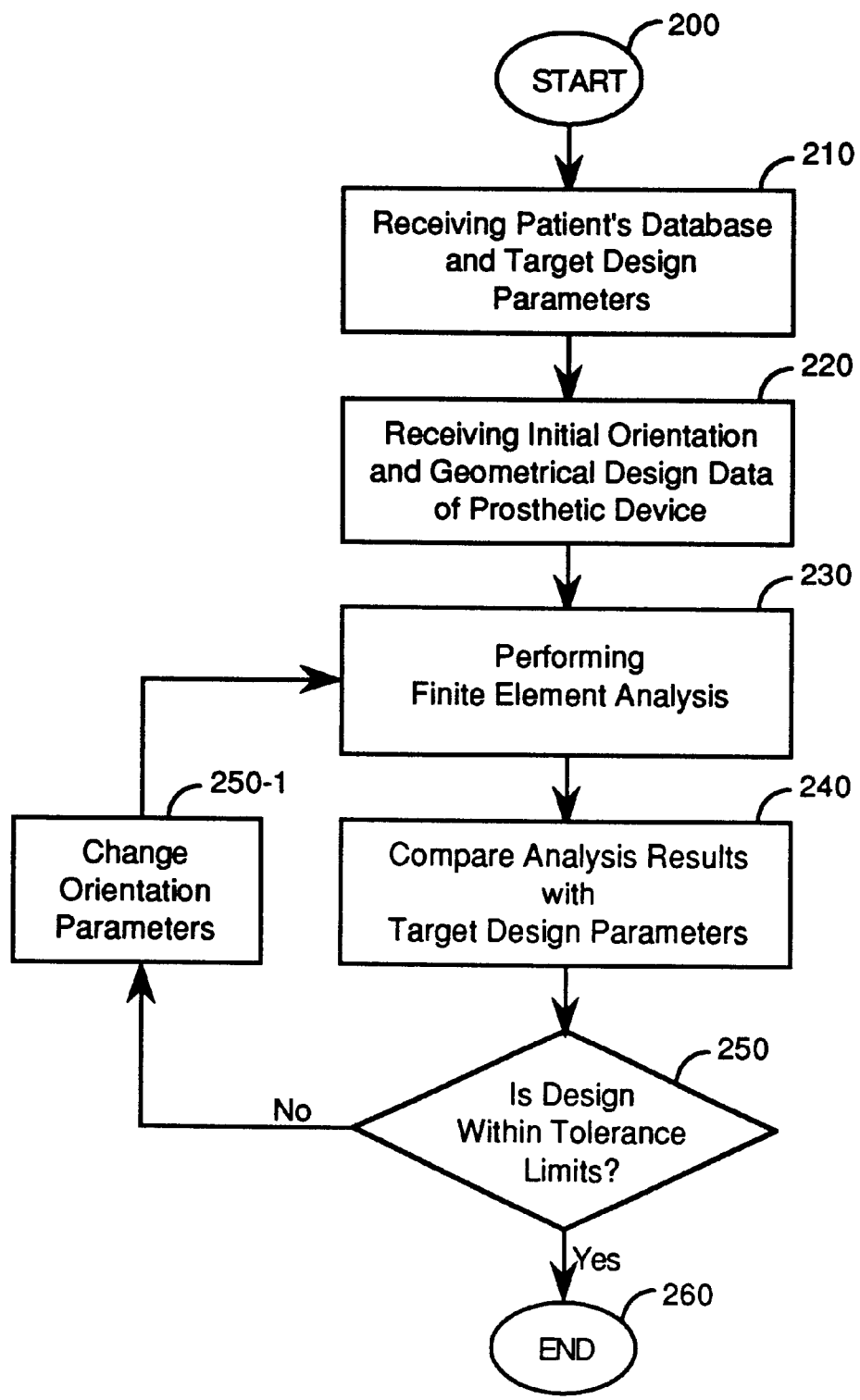
FIG. 7 is a flow chart showing the steps employed by the present invention for designing the unbalance composite prostheses.
Figure 11A:
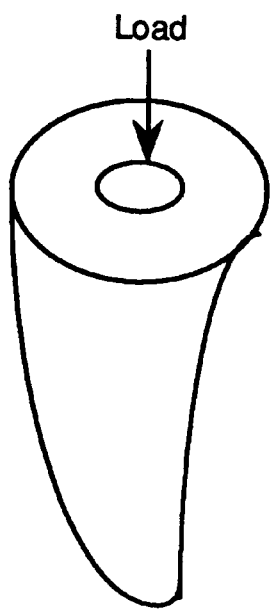
FIGS. 11A to 11D show the axial loading and coupling twisting and rotational movement of the unbalanced tubing-like and bend-plate design of the prosthetic devices of this invention.
Figure 11B:
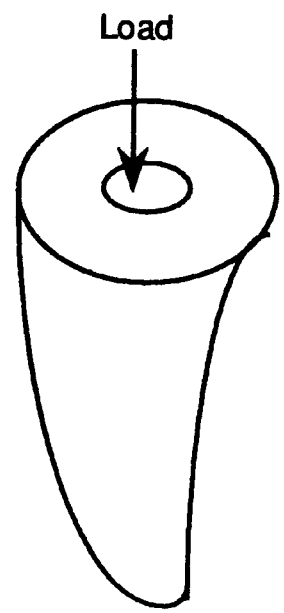
Figure 11C:
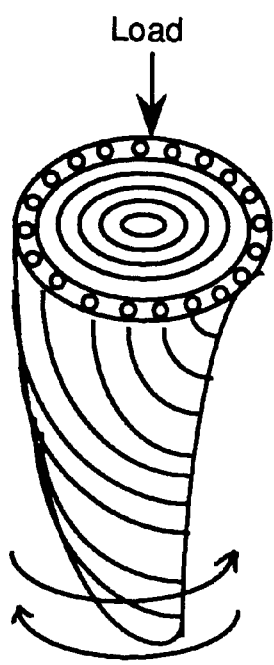
Figure 11D:
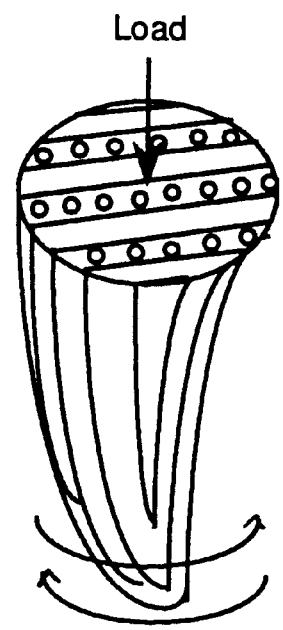

A flow chart is shown in FIG. 7 to illustrate a design process applying the stack sequence of ply-orientations as a design parameters. A prosthetic device with specific performance characteristics of stiffness, stress shielding, and micromotion can be obtained by employing the anisotropic nature of the ply orientations. The design process begins (step 200) with receiving patient's database (step 210) including the data for geometrical configuration of the bone, relative position of the bone in the body, the body weight, and data relating to stiffness, loading, mechanical movements, force transformation, strain and stress distributions, and other data to be employed in the design process. An initial set of ply orientations and geometrical design of the prosthesis is inputted (step 220). A finite element analysis is carried out to determine design parameters such implane bending, torsional load, micromotion and deformations, normal stress distribution, and strain energy density (step 230). The results of these design parameters are compared with a set of target performance parameters (step 240). Depending on the comparisons, a determination is made to change the design of the composite prosthesis including the orientations of the plies (step 250) for repeating the step of finite element analysis (step 230). The iterative design process ends when the design parameters are with tolerance ranges of the target parameters (step 260). The fiber orientations of each layer and the combined stack sequence thus provide a very useful design parameter for a prosthesis designer to systematically determine the most fitting device. The details of the finite element analyses and the data comparison processes are summarized in two papers submitted to be published. These two papers are incorporated herein as references and enclosed with this continuation-in-part (CIP) Application as reference attachments. A prior art U.S. Pat. No. 5,064,439 (Chang et al.) by the same inventor of the present invention is also incorporated herein as a reference to provide additional background information.

The present invention thus teaches a method for designing an unbalanced prosthetic device with a longitudinal direction including a plurality of plies wherein each ply being composed of a plurality of reinforced fibers aligned in a ply orientational angle $\theta_i$ relative to the longitudinal direction, where i=1,2,3, . . . ,N and N being the number of said plies. The design method including the steps of: (a) receiving a patient's database including relevant design data including geometrical configuration of a bone, relative position of a bone in a patient's body, a body weight, and data relating to stiffness, loading, mechanical movements, force transformation, strain and stress distributions; (b) receiving a set of target design parameters for the prosthetic device including targeted inplane bending, torsional load, micromotion and deformations, normal stress distribution, and strain energy density, and a set of design parameter tolerances; (c) receiving an initial set of orientational angles $\theta_i$ where i=1,2,3, . . . N; (d) performing a finite element analysis for determining a plurality of design parameters including inplane bending, torsional load, micromotion and deformations, normal stress distribution, and strain energy density; (e) comparing the design parameters from the finite element analysis with the target design parameters for determining if the design parameters being within the design parameter tolerances; (f) changing the ply orientational angles if the design parameters are not within the design parameter tolerances; and (g) repeating steps (c), (d) and (e) until the design parameters are within the design parameter tolerances.

For particular embodiments of the present invention, FIG. 8 shows the circumferetial displacement of several unbalanced-ply prostheses. FIGS. 9 and 10 show the circumferential shear strain medial bone and prosthesis interface for these prostheses. A composite hip prosthesis made of $((-10/-20)_s)_n$ layup produces the lowest bone prosthesis interface deformation and circumferential shear strain distribution. An unbalanced composite prosthesis with ply orientation in the range of near $((-10/-20)_s)_n$ would offer better performance than the balanced composite prostheses.

The circumferential shear strain at the interface between the implant prosthesis and the femur is directly related to the rotational micro-motions. The rotational motions thus become the most important motion component in the torsional fixation of an operation applying the total hip arthroplasty (THA). Based on the finite element analyses, the stiffness matrix for an angle-ply lamina is a full matrix where a sum of the terms Q16 and Q26 is a nonzero real number for an unbalanced composite. There exists a coupling between the longitudinal stress and shear deformation. Since the external joint forces involve both longitudinal and twisting load, the presence of the Q16 and Q26 terms in the composite stiffness matrix could improve both the longitudinal and the tosional responses of the implanting prosthetic device. Additional details can be referenced to the papers referenced above that was submitted together with the original Patent Application. More specifically, this invention discloses an unbalanced prosthetic device that has a material stiffness matrix with non-zero Q16 and Q26 terms. The prosthetic composite thus provides a twist coupling between the axial loading and the circumferential twist and rotation thus reduces the shear strain at the interface of the implant prosthesis and the femur. The prosthetic device of this invention provides an unbalanced composite having an angular inclination particular to a side effect of axial loading to produce specific coupling between the axial loading to the circumferential twisting and rotational movements. An acute angular inclination is side dependent based on the axial loading of a particular patient required to have the prosthetic implant.

FIGS. 11A to 11D are perspective view of the prosthetic device subject to axial loading with coupled twisting and rotational movements. The prosthetic composite can be tubing-like or bend-plate composite. The coupling movement can either be clockwise or counterclockwise depending on the axial loading and the side-dependent configuration of the implanted prosthesis.

Therefore, the present invention discloses a side-dependent prosthetic device which is a composite prosthetic device with a longitudinal direction. The composite prosthetic device includes a plurality of plies wherein each ply being composed of a plurality of reinforced fibers aligned in a ply orientational angle θi relative to the longitudinal direction of the prosthetic device, where i=1,2,3, . . . ,N and N being the number of the plies. The plurality of plies being laminated together for forming the prosthetic device wherein the ply orientational angles being arranged such that a sum of all the ply orientation angles represented by (θ1+θ2+θ3+ . . . +θ$_N$) is not zero thus forming an unbalanced composite prosthetic device. In another preferred embodiment, the ply orientational angles Oi forming a sequence which is represented by $((\theta^1/\theta^2)_s)_n$ where a first ply with orientational angle $\theta^1$ being followed by a second ply with orientational angle $\theta^2$ wherein such a sequence repeated n-times and arranged to be symmetrical to a mid-plane, wherein $\theta^1$ being an angle close to $-10_i$ and $\theta^2$ being an angle close to $-20_i$. In yet another preferred embodiment, the plurality of reinforced fibers being embedded in a matrix of biocompatible polymeric material.

Thus, the present invention provides a new prosthetic device and fabrication method which is anisotropic in nature and side-dependent in order to overcome the difficulties encountered in the prior art. Specifically, the present invention provides a prosthetic device which is designed and fabricated by a new method wherein the prosthetic device are fabricated by use of unbalanced oriented fiber composites such that it is side-dependent and the micromotion and stress shielding and caused by the mismatch due to side-dependent effects are minimized. Furthermore, the present invention provides a prosthetic design and fabrication method wherein design steps are disclosed to determine the orientations of prosthetic composites by taking into account of geometric variations and ply drop-offs due to termination such that the anisotropic nature of the fiber composites can be best utilized to tailor fit the implant variations. Additionally, the design method further determines the corresponding stress energy density (DEN) for the bone such that a long-term bone maintenance program can be properly established and implemented. More favorable stresses and deformation are generated in the femur with composite implants as compared to conventional metallic implants. In addition, by changing fiber orientations according to femoral loads utilizing unbalanced composites, a composite implant is produced specifically for the left or right femur. As the ply orientations in an unbalanced composite are used as a design parameter, the selection of the angles of the ply orientations may be flexibly made to tailor fit a patient depending on the age, sex, race and the specific configurations of right or left femurs.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

What is claimed is:

1. A composite prosthetic device provided for implanting in a femoral bone having a shaft and a neck, wherein said shaft oriented in a longitudinal stem-length direction defining a longitudinal axis and said neck extended from said shaft at a positive acute angle $\theta_{NECK}$ relative to said longitudinal axis, said prosthetic device comprising:

a plurality of plies wherein each ply being composed of a plurality of reinforcing fibers aligned in a ply orientational angle θi relative to said longitudinal axis where i=1, 2, 3, . . . ,N and N being the number of said plies;

said plurality of plies being laminated together for forming said prosthetic device wherein said ply orientational angles represented θ1, θ2, θ3, . . . , and θ$_N$, are negative acute angles with respect to said longitudinal axis wherein θ1+θ2,+θ3+ . . . +θ$_N$, is a none-zero negative value thus forming an unbalanced prosthetic device.

2. The composite prosthetic device of claim 1 wherein:

said ply orientational angles θi, where i=1,2,3, . . . ,N, forming a sequence represented by $((\theta^1/\theta^2)_s)_n$ where a first ply with orientational angle $\theta^1$ being followed by a second ply with orientational angle $\theta^2$ with such a sequence repeated n-times and arranged to be symmetrical to a mid-plane at about half-way between the two ply orientations wherein said $\theta^1$ being an angle close to $-10°$ and $\theta^2$ being an angle close to $-20°$ relative to said longitudinal axis wherein $n(\theta^1+\theta^2)$ is a none-zero negative value thus forming an unbalanced prosthetic device.

3. The composite prosthetic device of claim 2 wherein:

said plurality of reinforced fibers being embedded in a matrix of biocompatible polymeric material.

4. The composite prosthetic device of claim 1 wherein:

said plurality of plies composed of reinforcing fibers are bend plates composed of a plurality of bend reinforcing fibers aligned in a ply orientational angle $\theta i$ relative to said longitudinal axis running along said stem length of said prosthetic device, where i=1, 2, 3, . . . ,N and N being the number of said plies and said $\theta1+\theta2,+\theta3+ \ldots +\theta_N$, is a none-zero negative value thus forming an unbalanced prosthetic device.

5. The composite prosthetic device of claim 1 wherein:

said plurality of plies composed of reinforcing fibers are flat plates composed of a plurality of flat reinforcing fibers aligned in a ply orientational angle $\theta i$ relative to said longitudinal axis running along said stem length of said prosthetic device, where i=1, 2, 3, . . . ,N and N being the number of said plies and said $\theta1+\theta2,+\theta3+ \ldots +\theta_N$, is a none-zero negative value thus forming an unbalanced prosthetic device.

* * * * *